United States Patent [19]

Stähle et al.

[11] 4,361,575
[45] Nov. 30, 1982

[54] SUBSTITUTED 2-PHENYLAMINO-2-IMIDAZOLINES AND SALTS THEREOF

[75] Inventors: Helmut Stähle; Herbert Köppe; Werner Kummer, all of Ingelheim am Rhein, Fed. Rep. of Germany; Walter Kobinger, Vienna, Austria; Christian Lillie, Vienna, Austria; Ludwig Pichler, Vienna, Austria; Wolfgang Hoefke, Wiesbaden, Fed. Rep. of Germany; Wolfram Gaida, Ingelheim am Rhein, Fed. Rep. of Germany

[73] Assignee: Boehringer Ingelheim GmbH, Ingelheim am Rhein, Fed. Rep. of Germany

[21] Appl. No.: 276,703

[22] Filed: Jun. 23, 1981

Related U.S. Application Data

[63] Continuation-in-part of Ser. No. 208,519, Nov. 20, 1980, abandoned.

[30] Foreign Application Priority Data

Nov. 26, 1979 [DE] Fed. Rep. of Germany ....... 2947563

[51] Int. Cl.³ ................. C07D 233/06; A61K 31/415
[52] U.S. Cl. ................................ 424/273 R; 548/351
[58] Field of Search ..................... 548/351; 424/273 R

[56] References Cited

U.S. PATENT DOCUMENTS

| 3,708,485 | 1/1973 | Stähle et al. | 548/351 |
| 3,850,926 | 11/1974 | Stähle et al. | 424/273 R |
| 4,277,487 | 7/1981 | Stähle et al. | 548/351 |

*Primary Examiner*—Jane T. Fan
*Attorney, Agent, or Firm*—Hammond & Littell, Weissenberger & Muserlian

[57] ABSTRACT

Compounds of the formula

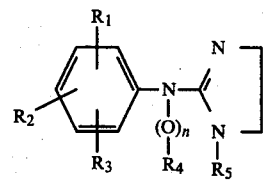

wherein
 $R_1$, $R_2$ and $R_3$, which may be identical to or different from each other, are each hydrogen, fluorine, chlorine, bromine, methyl, trifluoromethyl, hydroxyl or amino;
 $R_4$ is straight or branched alkyl of 1 to 5 carbon atoms, allyl or benzyl;
 $R_5$ is methyl, ethyl or 2-dimethylamino-ethyl; and
 n is 0 or 1;

and non-toxic, pharmacologically acceptable acid addition salts thereof. The compounds as well as their salts are useful as bradycardiacs.

3 Claims, No Drawings

SUBSTITUTED 2-PHENYLAMINO-2-IMIDAZOLINES AND SALTS THEREOF

This is a continuation-in-part of copending application Ser. No. 208,519, filed Nov. 20, 1980, now abandoned.

This invention relates to novel N-substituted 2-phenylamino-2-imidazolines and acid addition salts thereof, to methods of preparing these compounds, to pharmaceutical compositions containing them as active ingredients, and to methods of using them as bradycardiacs.

More particularly, the present invention relates to a novel class of 2-phenylamino-2-imidazolines represented by the formula

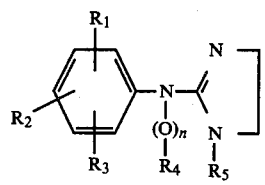

wherein
$R_1$, $R_2$ and $R_3$, which may be identical to or different from each other, are each hydrogen, fluorine, chlorine, bromine, methyl, trifluoromethyl, hydroxyl or amino;
$R_4$ is straight or branched alkyl of 1 to 5 carbon atoms, allyl or benzyl;
$R_5$ is methyl, ethyl or 2-dimethylamino-ethyl; and
n is 0 or 1;
and non-toxic, pharmacologically acceptable acid addition salts thereof.

The compounds embraced by formula I may be prepared by the following methods:

METHOD A

By reacting a 2-phenylamino-2-imidazoline of the formula

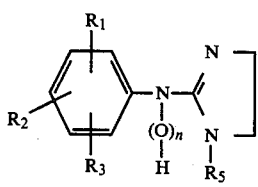

wherein $R_1$, $R_2$, $R_3$, $R_5$ and n have the same meanings as in formula I, with a halide of the formula $$Hal-R_4 \quad (III)$$

wherein
Hal is chlorine, bromine or iodine, and
$R_4$ has the meanings as in formula I.

When n is 0, the reaction is performed by heating a mixture of the reactants to a temperature of 40° to 150° C., preferably in the presence of a polar or non-polar solvent.

When n is 1, the reaction is performed at room temperature, and the halide of the formula III is reacted with the sodium salt of the compound of the formula II.

The specific reaction conditions depend to a large extent upon the reactivity of the individual reactants. In general, it is recommended to provide the halide in excess and to perform the reaction in the presence of an acid-binding agent.

METHOD B

By reacting a compound of the formula

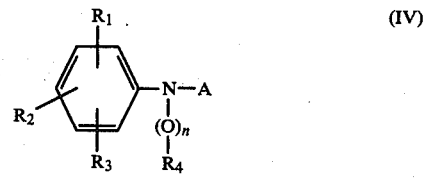

wherein
$R_1$, $R_2$, $R_3$, $R_4$ and n have the same meanings as in formula I, and
A is cyano or

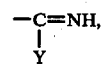

where Y is alkoxy of 1 to 4 carbon atoms, (alkyl of 1 to 4 carbon atoms)-thio, sulfhydryl or amino, with an alkylenediamine of the formula $$H_2N-CH_2-CH_2-NH-R_5 \quad (V)$$

wherein $R_5$ has the same meanings as in formula I.

The reaction is carried out at elevated temperatures between 60° and 180° C. The presence of a solvent is not required, although one may be used if desired.

METHOD C

By reacting an imidazoline derivative of the formula

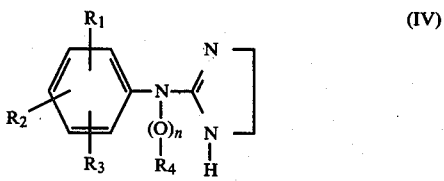

wherein $R_1$, $R_2$, $R_3$, $R_4$ and n have the same meanings as in formula I, or an anion thereof, with a halide of the formula $$Hal-R_5 \quad (VII)$$

wherein
Hal is chlorine, bromine or iodine, and
$R_5$ has the same meanings as in formula I.

The reaction is performed at elevated temperatures, advantageously between 40° and 120° C., and in the presence of a polar or non-polar solvent.

In a preferred embodiment of the reaction, the imidazoline derivative is converted into an anion with the aid of a basic substance, such as sodium hydride, and the anion is then reacted with the halide of the formula VII in the presence of an inert solvent such as tetrahydrofuran, dioxane, dibutyl ether or the like.

The starting compounds of the formulas II, IV, V and VI are described in the literature [see, for example, Belgian Pat. No. 623,305; German Offenlegungsschrift No. 2,457,979; Chem. Ber. 107, 2644 (1974); and Liebigs. Ann. Chem. 751, 159 (1971)]. The starting compounds of the formulas III and VII are obtained by halogenating the corresponding alcohols.

The compounds embraced by formula I are basic substances and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicyclic acid, ascorbic acid, methane-sulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-Methyl-2-[N-allyl-N-(2,6-dichloro-phenyl)-amino]-2-imidazoline by method A

A mixture consisting of 4.9 gm (0.02 mol) of 1-methyl-2-(2,6-dichlorophenyl-imino)-imidazolidine, 2.1 ml of allyl bromide (125% of the stoichiometrically required amount), 2.7 gm of sodium carbonate and 25 ml of ethanol was refluxed for 5.5 hours while stirring. Thereafter, the reaction mixture was filtered, the filtrate was evaporated in vacuo to dryness, the residue was dissolved in dilute (about 1 N) hydrochloric acid, and the resulting solution was extracted with ether (the ethanol extracts were discarded). The acidic aqueous phase was then fractionally extracted with ether at stepwisely increasing pH-values (addition of 2 N sodium hydroxide). The thin-layer chromatographically uniform fractions were combined, dried over magnesium sulfate, and the ether was evaporated in vacuo, leaving an oil which crystallized gradually throughout. 2.3 gm (40.5% of theory) of the compound of the formula

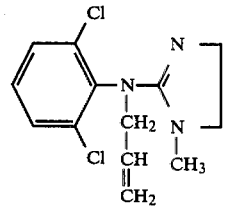

having a melting point of 59°–61° C. were obtained.

EXAMPLE 2

1-Methyl-2-[N-allyl-N-(2,6-dichloro-phenyl)-amino]-2-imidazoline by method C

A mixture consisting of 2.7 gm (0.01 mol) of 2-[N-allyl-N-(2,6-dichloro-phenyl)-amino]-2-imidazoline, 0.44 gm of a 55% sodium hydride dispersion and 25 ml of absolute tetrahydrofuran was refluxed for 5.5 hours while stirring, and the reaction mixture was allowed to stand overnight at room temperature. Thereafter, 1 ml of methyl iodide (about 160% of the stoichiometrically required amount) was added, and the mixture was refluxed for two hours. The reaction mixture was then evaporated to dryness in vacuo, the residue was dissolved in dilute (about 1 N) hydrochloric acid, and the resulting solution was extracted several times with ether (the ethereal extracts were discarded). The aqueous acidic phase was fractionally extracted with ether at stepwisely increasing pH-values (addition of 2 N sodium hydroxide). The thin-layer chromatographically uniform fractions were combined, dried over magnesium sulfate, and the ether was evaporated in vacuo, leaving 0.65 gm (23.0% of theory) of an initially oily residue which crystallized after a short period of time. The crystalline product had a melting point of 59°–61° C.

The identity of the end product of this example with that of Example 1 was established by thin-layer chromatogram and by IR-, NMR- and mass spectra.

EXAMPLE 3

1-Ethyl-2-[N-(2,6-dichloro-phenyl)-N-(n-propyl)-amino]-2-imidazoline and its hydrobromide by method A A mixture consisting of 5.2 gm (0.02 mol) of 1-ethyl-2-(2,6-dichlorophenyl-imino)-imidazoline, 2.7 ml (150% of the stoichiometrically required amount) of n-propyl-bromide, and 25 ml of acetonitrile was heated for 15 hours at 120° C. in a closed tube. Thereafter, the reaction mixture was evaporated to dryness in vacuo, the oily residue was dissolved in dilute (about 1 N) hydrochloric acid, and the resulting solution was extracted with ether (the ethereal extract was discarded). The acidic aqueous phase was fractionally extracted with ether at stepwisely increasing pH-values (addition of 2 N sodium hydroxide), whereby about ten ether fractions were obtained. Those fractions which contained the desired reaction product in pure form, as determined by thin-layer chromatography, were combined, dried over magnesium sulfate and evaporated in vacuo. The oily residue, 1-ethyl-2-[N-(2,6-dichloro-phenyl)-N-(n-propyl)-amino]-2-imidazoline base, was dissolved in a little methanol, the resulting solution was admixed with concentrated hydrobromic acid until it reacted acid to Congo red, and ether was added until crystallization was complete. 3.0 gm (39.4% of theory) of the hydrobromide of the formula

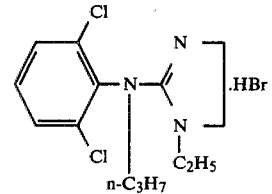

having a melting point of 196°–197° C. were obtained.

| Elemental analysis: | | | | |
|---|---|---|---|---|
| $C_{14}H_{19}Cl_2N_3 \cdot HBr$ (381.15) | | | | |
| | C | H | Halogen | N |
| Calculated: | 44.12% | 5.29% | 39.57% | 11.02% |
| Found: | 44.21% | 5.26% | 39.20% | 11.01% |

The following compounds of the formula

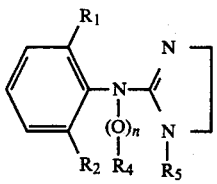

were prepared by method A in analogous manner:

B = 1-ethyl-2-[N-allyl-N-(2,6-dichloro-phenyl)-amino]-2-imidazoline, described in Example 11;
C = 2-[N-allyl-N-(2,6-dichloro-phenyl)amino]-2-imidazoline, disclosed in Example 1 of U.S. Pat. No. 3,708,485; and
D = 2-[N-(β-methyl-allyl)-N-(2,6-dichloro-phenyl)-amino]-2-imidazoline, disclosed in Example 1 of U.S. Pat. No. 3,850,926.

| Example No. | Form | $R_1$ | $R_2$ | n | $R_4$ | $R_5$ | Yield (% of theory) | M.p. (°C.) |
|---|---|---|---|---|---|---|---|---|
| 4 | base | —Cl | —Cl | 1 | —CH$_2$—CH=CH$_2$ | —CH$_3$ | 39.5 | 64 |
| 5 | hydrobromide | —Cl | —Cl | 0 | -n-C$_4$H$_9$ | —CH$_3$ | 21.0 | 219–220 |
| 6 | hydrobromide | —Cl | —Cl | 0 | —CH$_2$—CH$_2$—CH(CH$_3$)$_2$ | —CH$_3$ | 26.6 | 225–227 |
| 7 | hydrobromide | —Cl | —Cl | 0 | -n-C$_5$H$_{11}$ | —CH$_3$ | 43.6 | 124–126 |
| 8 | hydrobromide | —Cl | —Cl | 0 | -n-C$_3$H$_7$ | —CH$_3$ | 47.7 | 208–209 |
| 9 | base | —Cl | —Cl | 0 | —CH$_2$—C$_6$H$_5$ | —CH$_3$ | 33.7 | 122 |
| 10 | hydrobromide | —Cl | —Cl | 0 | -n-C$_4$H$_9$ | —C$_2$H$_5$ | 34.2 | 200 |
| 11 | hydrobromide | —Cl | —Cl | 0 | —CH$_2$—CH=CH$_2$ | —C$_2$H$_5$ | 53.4 | 178 |
| 12 | hydrobromide | —Cl | —Cl | 0 | —CH$_2$—CH$_2$—CH(CH$_3$)$_2$ | —C$_2$H$_5$ | 16.5 | 165–167 |
| 13 | hydrobromide | —Br | —Br | 0 | -n-C$_4$H$_9$ | —CH$_3$ | 46.8 | 225–226 |
| 14 | hydrobromide | —Br | —Br | 0 | —CH$_2$—CH=CH$_2$ | —CH$_3$ | 58.7 | 171–173 |
| 15 | hydrobromide | —Br | —Br | 0 | -n-C$_3$H$_7$ | —CH$_3$ | 45.3 | 202–203 |
| 16 | hydrobromide | —Br | —Br | 0 | -n-C$_5$H$_{11}$ | —CH$_3$ | 42.7 | 156–157 |
| 17 | hydrobromide | —Br | —F | 0 | -n-C$_4$H$_9$ | —CH$_3$ | 50.0 | 183–184 |
| 18 | hydrobromide | —Br | —F | 0 | -n-C$_3$H$_7$ | —CH$_3$ | 47.5 | 207–209 |
| 19 | hydrobromide | —Br | —F | 0 | —CH$_2$—CH=CH$_2$ | —CH$_3$ | 39.5 | 144–146 |
| 20 | hydrobromide | —Br | —F | 0 | -n-C$_5$H$_{11}$ | —CH$_3$ | 35.5 | 151–152 |
| 21 | hydrobromide | —F | —CF$_3$ | 0 | -n-C$_3$H$_7$ | —CH$_3$ | 27.3 | 214 |
| 22 | hydrobromide | —F | —CF$_3$ | 0 | -n-C$_4$H$_9$ | —CH$_3$ | 28.2 | 164–166 |
| 23 | base | —F | —CF$_3$ | 0 | -n-C$_5$H$_{11}$ | —CH$_3$ | 28.2 | oily |
| 24 | base | —Cl | —Cl | 0 | -n-C$_3$H$_7$ | —CH$_2$—CH$_2$—N(CH$_3$)$_2$ | 39.3 | oily |
| 25 | hydrochloride | —Cl | —Cl | 0 | -n-C$_4$H$_9$ | —CH$_2$—CH$_2$—N(CH$_3$)$_2$ | 48.3 | oily |
| 26 | hydrobromide | —Cl | —Cl | 0 | —CH$_2$—CH=CH$_2$ | —CH$_2$—CH$_2$—N(CH$_3$)$_2$ | 42.3 | oily |

The compounds of the present invention, that is, those embraced by formula I above and their non-toxic, pharmacologically acceptable acid addition salts, have useful pharmacodynamic properties. More particularly, they exhibit bradycardiac activity in warm-blooded animals such as rats and rabbits.

The bradycardiac activity of the compounds of the present invention and of closely related compounds disclosed in the prior art was ascertained by determining the dose which reduces the heart rate of spinal rats by 150 beats/minute. The following table shows the results obtained, where A = 1-methyl-2-[N-allyl-N-(2,6-dichloro-phenyl)-amino]-2-imidazoline, described in Example 1;

| Compound | $D_{150}$ mgm/kg |
|---|---|
| Invention: | |
| A | 1.8 |
| B | 1.45 |
| Prior Art: | |
| C | 2.5 |
| D | 7.0 |

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0014 to 1.14 mgm/kg body weight, preferably 0.014 to 0.42 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 27

Coated tablets

The tablet core composition is compounded from the following ingredients:

| | |
|---|---|
| 1-Methyl-2-[N—allyl-N—(2,6-dichloro-phenyl)-amino]-2-imidazoline | 5 parts |
| Lactose | 65 parts |
| Corn starch | 130 parts |
| Sec. calcium phosphate | 40 parts |
| Soluble starch | 3 parts |
| Magnesium stearate | 3 parts |
| Colloidal silicic acid | 4 parts |
| Total | 250 parts |

Preparation:

The active ingredient is admixed with a portion of the excipient, the mixture is thoroughly kneaded with an aqueous solution of the soluble starch, and the moist mass is granulated by passing it through a screen. The granulate is dried, admixed with the remainder of the excipient, and the composition is compressed into 250 mgm-tablet cores which are subsequently coated with a thin shell consisting essentially of a mixture of sugar, talcum and gum arabic. Each coated tablet is an oral dosage unit composition containing 5 mgm of the active ingredient.

EXAMPLE 28

Hypodermic solution

The solution is compounded from the following ingredients:

| | |
|---|---|
| 1-Methyl-2-[N—allyl-N—(2,6-dichloro-phenyl)-amino]-2-imidazoline | 1.0 parts |
| Sodium chloride | 18.0 parts |
| Distilled water q.s.ad | 2000.0 parts by vol. |

Preparation

The active ingredient and the sodium chloride are dissolved in the distilled water, the solution is filtered until free from suspended particles, and the filtrate is filled into 2 cc-ampules in an atmosphere of nitrogen. The contents of each ampule are an injectable dosage unit composition containing 1 mgm of the active ingredient.

EXAMPLE 29

Drop solution

The solution is compounded from the following ingredients:

| | |
|---|---|
| 1-Methyl-2-[N—allyl-N—(2,6 dichloro-phenyl)-amino]-2-imidazoline | 0.02 parts |
| Methyl p-hydroxy-benzoate | 0.07 parts |
| Propyl p-hydroxy-benzoate | 0.03 parts |
| Demineralized water q.s.ad | 100 parts by vol. |

Preparation:

The active ingredient and the p-hydroxy-benzoates are dissolved in the demineralized water, the resulting solution is filtered, and the filtrate is filled into 100 ml-bottles equipped with a dropping spout. 5 ml (about 20 drops) of the solution are an oral dosage unit composition containing 1 mgm of the active ingredient.

Any one of the other compounds embraced by formula I or a non-toxic, pharmacologically acceptable acid addition salt thereof may be substituted for the particular active ingredient in Examples 27 through 29.

Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 1-Ethyl-2-[N-(n-propyl)-N-(2,6-dichloro-phenyl)amino]-2-imidazoline or a non-toxic, pharmacologically acceptable acid addition salt thereof.

2. A bradycardiac pharmaceutical dosage unit composition consisting essentially of an inert pharmaceutical carrier and an effective bradycardiac amount of a compound of claim 1.

3. The method of slowing the heart rate of a warm-blooded animal in need thereof, which comprises perorally, parenterally or rectally administering to said animal an effective bradycardiac amount of a compound of claim 1.

* * * * *

UNITED STATES PATENT AND TRADEMARK OFFICE
CERTIFICATE OF CORRECTION

PATENT NO. : 4,361,575
DATED : November 30, 1982
INVENTOR(S) : HELMUT STÄHLE ET AL.

It is certified that error appears in the above-identified patent and that said Letters Patent is hereby corrected as shown below:

Column 2, line 43: The structural formula "IV" of Method C should be designated as formula -- VI --.

Column 3, line 19: "salicyclic" should read -- salicylic --.

Column 8, line 43: "(2,6-dichloro-phenyl-" should read -- (2,6-dichloro-phenyl)- --.

Column 8 line 44: Delete ")".

Signed and Sealed this

First Day of March 1983

[SEAL]

Attest:

Attesting Officer

GERALD J. MOSSINGHOFF
Commissioner of Patents and Trademarks